United States Patent [19]
Lataix

[11] Patent Number: 5,158,192
[45] Date of Patent: Oct. 27, 1992

[54] DISPENSING BOTTLE WITH COUPLING BETWEEN CLOSURE HEAD AND SCREW CAP

[75] Inventor: Gilbert Lataix, Chatel-Guyon, France

[73] Assignee: Laboratoires Merck Sharp & Dohme-Chibret, Paris, France

[21] Appl. No.: 602,836

[22] Filed: Oct. 24, 1990

[30] Foreign Application Priority Data

Oct. 26, 1989 [FR] France ................. 89 14046

[51] Int. Cl.$^5$ .................. B65D 1/02; B65D 1/08; B65D 47/10; B29C 49/18
[52] U.S. Cl. ..................... 215/32; 215/256; 220/258; 222/541
[58] Field of Search ............... 222/420, 421, 541, 212; 215/32, 308, 31, 33, 256; 220/258

[56] References Cited

U.S. PATENT DOCUMENTS

| | | |
|---|---|---|
| 2,162,752 | 6/1939 | Schauer . |
| 4,157,765 | 6/1979 | Golebiewsky ............ 220/258 X |
| 4,402,415 | 9/1983 | Hopley ..................... 215/32 |
| 4,467,930 | 8/1984 | Schnell et al. ............. 215/32 |
| 4,526,279 | 7/1985 | Weiler et al. .............. 215/32 |
| 4,602,638 | 11/1986 | Schmidt ................. 215/32 X |
| 4,655,355 | 4/1987 | Turoff et al. .............. 215/32 |
| 4,688,703 | 8/1987 | Bayer .................... 220/258 X |
| 4,747,501 | 5/1988 | Greaues ................. 215/32 X |
| 4,773,548 | 9/1988 | Deussen ................. 215/32 X |
| 4,821,897 | 4/1989 | Weiler ....................... 215/32 |
| 5,007,546 | 4/1991 | Rose et al. ................. 215/32 |

FOREIGN PATENT DOCUMENTS

| | | |
|---|---|---|
| 0119145 | 9/1984 | European Pat. Off. . |
| 0137458 | 4/1985 | European Pat. Off. . |
| 0312725 | 4/1989 | European Pat. Off. . |
| 2252649 | 5/1973 | Fed. Rep. of Germany ........ 215/32 |
| 2332155 | 1/1975 | Fed. Rep. of Germany ........ 215/32 |
| 3733713 | 4/1989 | Fed. Rep. of Germany ...... 220/258 |
| 1417219 | 10/1965 | France .................... 220/258 |
| 2565939 | 12/1985 | France . |
| 89/00534 | 1/1989 | PCT Int'l Appl. . |

*Primary Examiner*—Sue A. Weaver
*Attorney, Agent, or Firm*—William H. Nicholson; Joseph F. DiPrima

[57] ABSTRACT

A sterile packaging assembly (100) for dispensing a liquid in drops comprises a main body (101) of plastic material, having a top portion (103) with an outside thread for receiving a screw cap (104), the top portion ending in an elongate neck, constituting a dispensing portion which is surmounted by a closure head (110) that can be torn off in order to define a dispensing orifice (111) on first utilization of the packaging assembly. The invention is particularly applicable to sterile packaging of pharmaceutical substances such as eye drops.

5 Claims, 6 Drawing Sheets

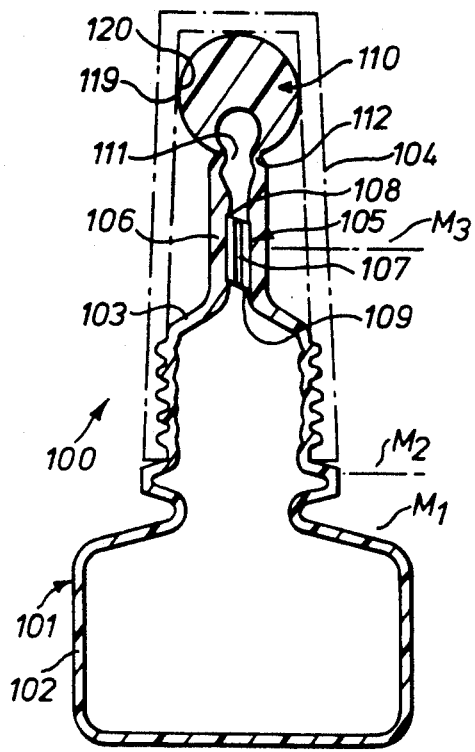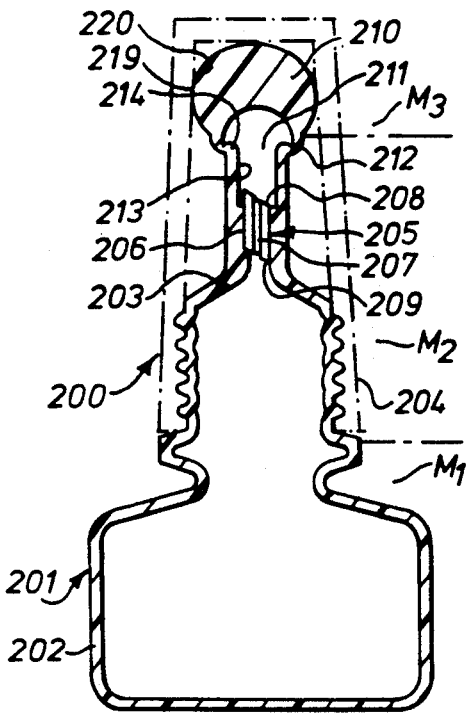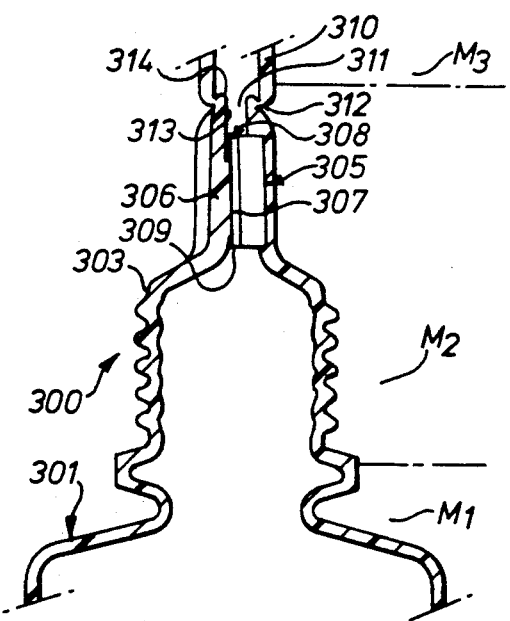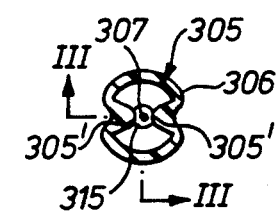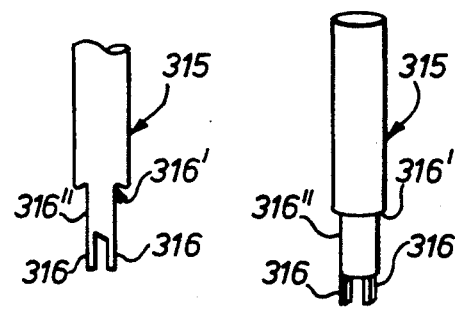

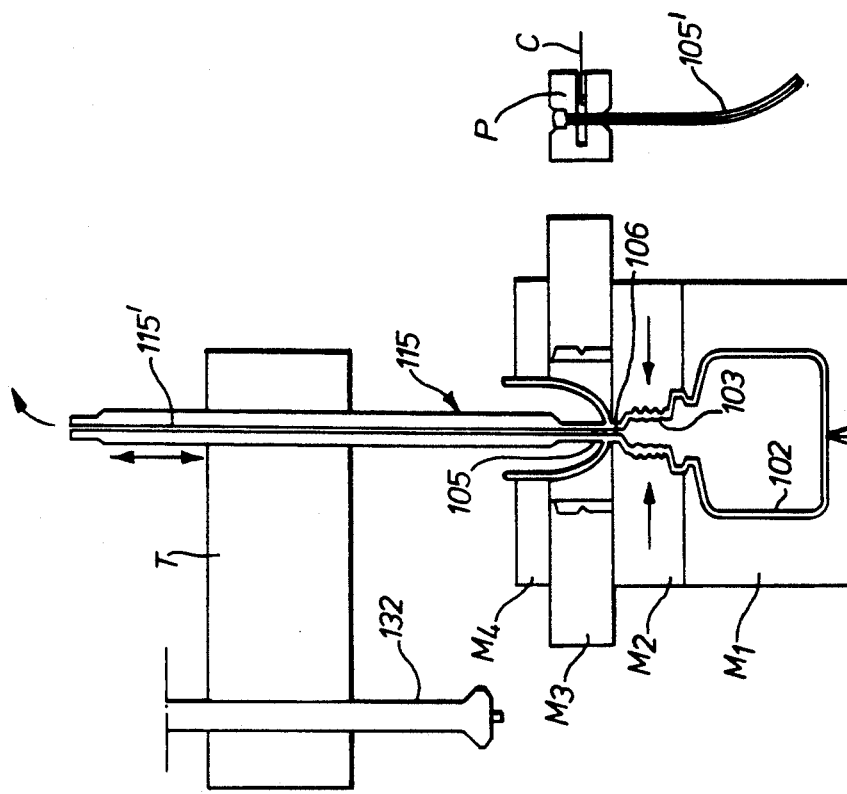
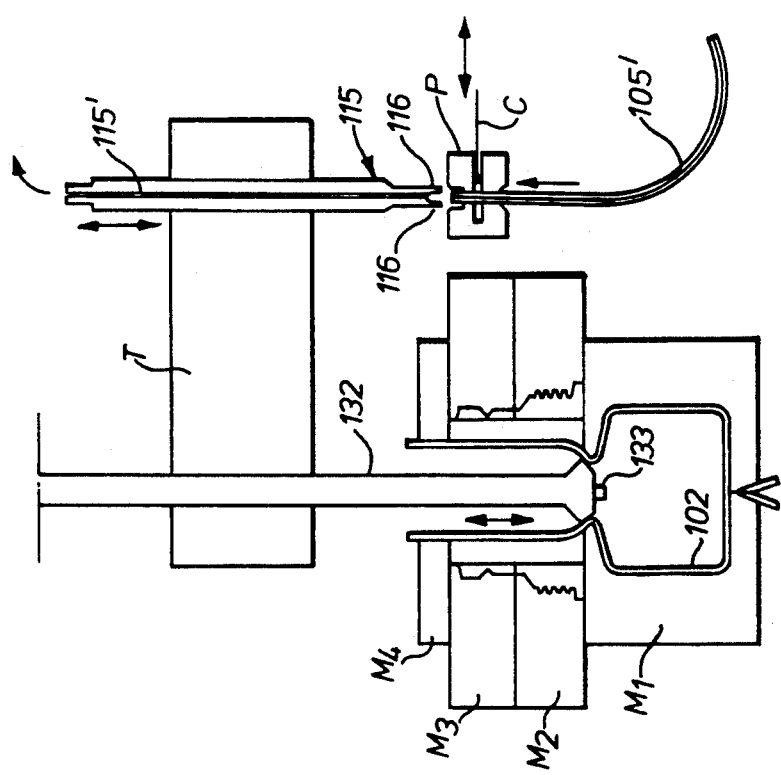

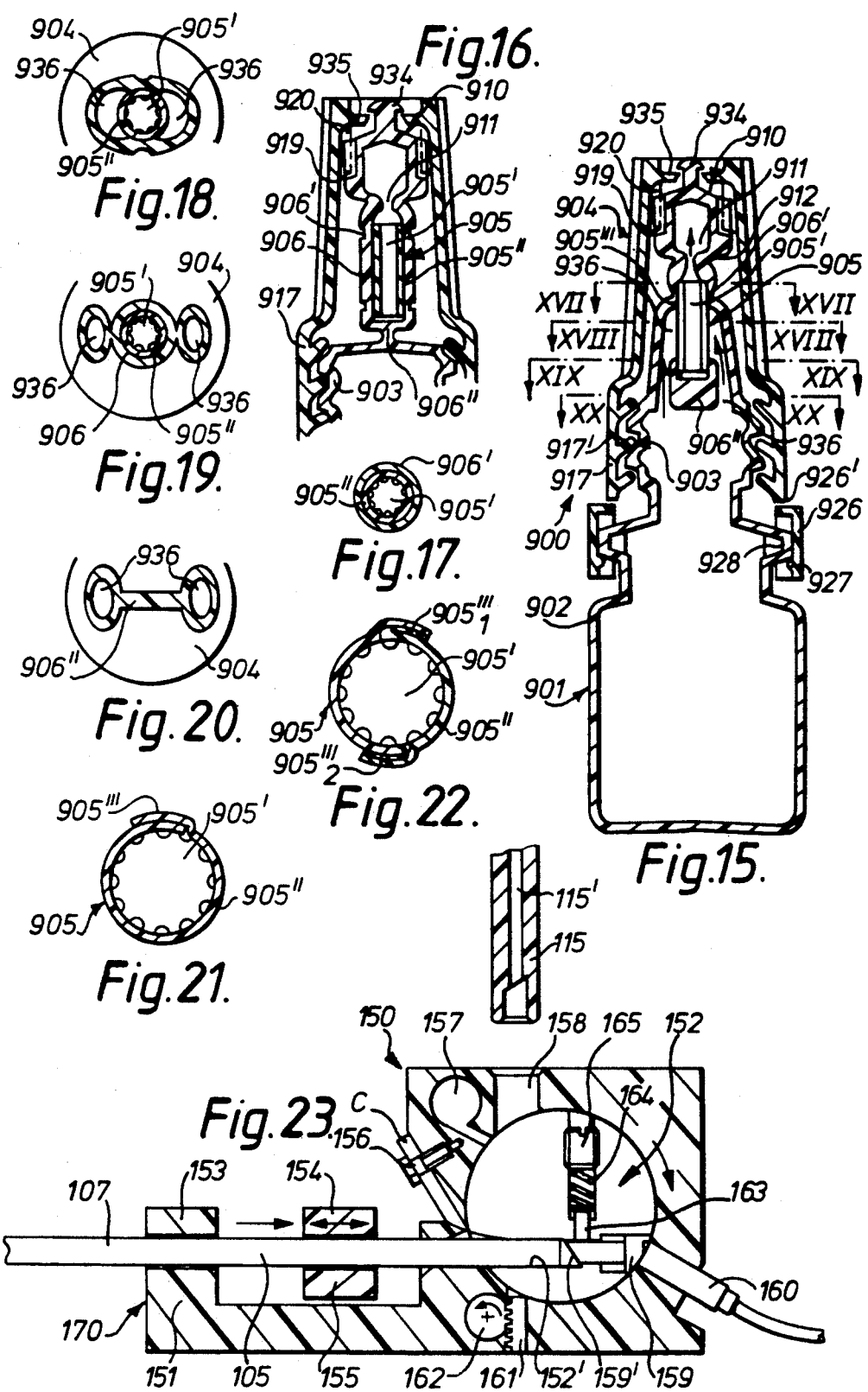

DISPENSING BOTTLE WITH COUPLING BETWEEN CLOSURE HEAD AND SCREW CAP

The invention relates to the field of sterile packaging of liquid, and more particularly to packaging assembles allowing a liquid to be dispensed in drops.

A typical case is that of the sterile and tamperproof packaging of eye drops, where the packaging assembly should permit easy dispensing in drops, in particular in regular drops and without any jet.

This problem is well known to specialists, and many solutions have already been proposed.

A first type of proposed solution concerns the techniques for manufacturing packaging assemblies which specialists in the field generally refer to as "bottle packs".

One such technique is illustrated, for example, in U.S. Pat. Nos. 3,919,374 and 4,176,153.

The pre-form is first extruded, and then the bottle is blown after closure; the bottle thus formed (not yet finished) is then filled, generally using a needle, and finally sealed (this last operation being carried out using a complementary upper mould).

This technique is completely satisfactory as regards the production of sterile packaging assemblies, with or without tamperproofing.

However, it is unsuitable for a satisfactory dispensing in drops.

In this case, use is in fact made of a capsule or cap having an internal central perforating pin; the hole thus formed in the body of the packaging assembly does not permit a regular drop formation (the latter depends to a considerable extent on the pressure exerted by the user on the packaging assembly), and moreover the jet of liquid is uncoordinated.

In a variant, it has been proposed to replace the capsule-and-pin system by a tear-off closure head on which a screw cap is arranged (see, for example, U.S. Pat. No. 4,378,891). In order to gain access to the stopper of the packaging assembly, it is necessary to screw the cap, which results in a lifting of the closure head (by an abutment of the lower edge of the cap on an associated shoulder on the body of the packaging assembly) and the detachment of the closure head: the structure of this packaging assembly is therefore complex, and its implementation at the time of the first use is relatively complicated (the screwing of the cap is in particular unnatural for the user). Moreover, the orifice obtained necessarily has a relatively large diameter (otherwise there would be a risk of the outlet channel being blocked). The flow rate is therefore still very irregular, and the jet is relatively uncoordinated.

Another type of proposed solution has consisted in using a prefabricated subassembly forming an end-piece and stopper.

The advantage lies in the accuracy of the subassembly which is manufactured beforehand by injection.

Thus, French Patent No. 2,511,973 illustrates several solutions of this type.

In order to form such packaging assemblies, a conventional blowing operation is first carried out (generally of the "bottle pack" type), then filling; the end-piece/stopper subassembly is then put into position, and the operation is finished by sealing the upper part, which at the same time results in the fixing of the said subassembly (in the manner of hot forming).

Sometimes sealing concerns only the lower part of the end-piece/stopper subassembly (see, for example, FIGS. 9 to 11 in French Patent No. 2,511,973), which has the disadvantage that opening and closing of the stopped remain possible. The simple screw cap can be associated with a tear-off ring (see, for example, FIGS. 20 and 21 in French Patent No. 2,511,973). The sealing may also concern the entire end-piece/stopper subassembly ensuring that a kind of tear-off cocoon is obtained surrounding the said subassembly, which makes it possible to avoid the abovementioned disadvantage (see, for example, FIGS. 26 and 28 in French Patent No. 2,511,973). In a variant (see, for example, FIGS. 30 and 33 in French Patent No. 2,511,973), it is possible to provide a screw cap on a tear-off head: access to the outlet end-piece and/or to the stopper of the packaging assembly requires a screwing of the cap, which results in a lifting of the closure head and a detachment of the latter (as for the abovementioned system described in U.S. Pat. No. 4,378,891): here again, the structure is very complex, and the implementation at the time of the first use is relatively complicated.

Such techniques using prefabricated subassemblies remain expensive anyway (it is necessary to produce two pieces injected separately, then to assemble them, while at the same time adhering to the required conditions of cleanliness).

Another important disadvantage lies in the imperfect nature of the leakproofness.

As has been stated hereinabove, if the end-piece with its stopper is directly accessible, there is a risk that the product will no longer be sterile upon storage of the packaging assembly: this results in particular from the risk of the subassemblies becoming unscrewed while being conveyed (for example by the vibratory hopper feeder) and/or during their positioning. If a cocoon is provided, it must constitute a detachable closure head, which means that a tearing zone must be provided so that the patient can open the bottle, in other words an interrupted connection with bridges: this always results in a risk of leakage to a greater or lesser extent.

Moreover, everyone knows that a hot-forming technique is difficult to control (for example, material variations render the hot forming imperfect): this not only results in a second risk of leakage, but also a risk that the product is no longer sterile (which unfortunately is not always visible from the outside).

All in all, these techniques using prefabricated subassemblies are expensive and unsatisfactory as regards the leakproofness, and even the sterility.

Mention may also be made of analogous techniques using an add-on stopper (see, for example, U.S. Pat. No. 4,226,334) with, optionally, a head which can be torn off by lifting (see, for example, PCT Patent Application No. WO 85/00,340) with the same disadvantages as those which have just been described.

A third type of proposed solution has consisted in forming, in the head of the packaging assembly, a channel of very small diameter (the specialists refer in this case to a microchannel, since the diameters involved are of the order of one to three tenths of a millimeter), this head being closed by a simple screw cap.

U.S. Pat. No. 4,584,823 thus illustrates a solution of this type, in which a very fine needle is used to produce the microchannel.

In order to manufacture such packaging assemblies, a blowing operation and a filling operation are first carried out, as above, using a mandrel which is here mounted on a drum with a vertical axis; the mandrel is then lifted up, and the drum is then turned in order to bring the needle and its support into the axis of the partially formed main body: the needle is then put into position in an intermediate stand-by mould, which mould is then closed for the continuation of the process, which is the production of the dispensing end-piece.

Furthermore, it has recently been proposed to improve this technique by providing two intermediate moulds (the assembly is then entirely closed by virtue of the third mould).

This technique nevertheless remains very difficult to implement, in particular because of the fragility of the needle. The needle may break or twist (if it breaks, there is no hole, and if it twists, there is a risk of leakage): this means that a permanent monitoring of the needle must be carried out in order to verify its condition, since it is difficult to verify that the hole does indeed exist and/or that the leakproofness is satisfactory.

Finally, mention may be made, for the record, of other techniques which are more remote, but which illustrate well the wide variety of the solutions proposed: these techniques are described in PCT Patent Application No. WO 86/00,598, British Patent No. 2,053,866, U.S. Pat. Nos. 2,893,613 and 2,324,237, and German Patent No. 1,813,047.

The principal aim of the present invention is to provide a sterile packaging assembly which does not have the abovementioned disadvantages and which makes it possible, more especially, to avoid any risk of defective leakproofness capable of spoiling the sterility.

Another aim of the invention is to produce a packaging assembly making it possible to obtain a regular drop formation without a jet.

Another aim of the invention is to produce a packaging assembly which is simple for the patient to use, even in the case of elderly persons.

Another aim of the invention is to produce a packaging assembly of simple structure, and to implement an associated manufacturing method which is simple and advantageous with respect to production costs.

The invention relates more particularly to a sterile packaging assembly allowing a liquid to be dispensed in drops, characterized by the fact that it comprises a main body of plastic material whose upper part, threaded externally in order to receive a screw cap, ends in a narrower elongate neck constituting a dispensing portion, the said dispensing portion being surmounted by a closure head which can be torn off in order to define a dispensing orifice, rotational coupling means being additionally provided between the outer surface of the closure head and the adjacent inner surface of the screw cap, the said coupling means allowing the said closure head to be detached by unscrewing the said cap upon the first use of the said packaging assembly.

According to a first embodiment, the closure head is wider than the elongate neck and has a general flattened shape presenting an outer surface adjacent to the opposite inner surface of the screw cap, a rigid connection, preferably by gluing or welding effected between the said surfaces after the positioning of the said screw cap, being additionally provided in order to define the coupling between the said closure head and the said screw cap.

According to another embodiment, affording an improved rotational coupling, the closure head has an outer surface externally toothed in such a way as to cooperate with a homologous inner toothing of the screw cap in order to detach the said closure head by unscrewing the said cap; in particular, the associated toothings of the closure head and of the screw cap are in the form of axial flutings.

In addition, advantageously, the packaging assembly of the invention comprises a snap-locking means between the screw cap and the closure head, allowing the said closure head to be retained once torn off in the said cap after unscrewing of the latter.

For example, the snap-locking means essentially consists of radial fins surmounting the closure head, and of which the radially outside edge forms a lug co-operating with an annular rim formed in the inner surface of the screw cap; in particular, it will be possible to provide two radial fins situated in the joint plane of the mould used to form the main body.

In a variant, the snap-locking means essentially consists of an upper point in the form of an arrow surmounting the closure head, able to co-operate with transverse lugs or a transverse base of the screw cap.

According to the first embodiment, the screw cap is monobloc and has, at the lower end, a flexible thread which can move aside upon fitting by pressure, when the said assembly is being put together, in contact with the outer threading of the upper part of the main body.

According to another embodiment, the screw cap is in two parts which can be connected to each other by axial snap-locking, namely a main part threaded internally in order to be screwed normally, when the said assembly is being put together, on the upper part of the main body, and a second part forming a closure cap, the said second part presenting the toothed portion cooperating with the outer toothing of the closure head, a rotary drive connection being additionally provided between the said parts constituting the said screw cap.

Advantageously, in this case, the second part forming the closure cap has a cylindrical sleeve penetrating into the main part of the cap, the said sleeve being toothed internally in order to co-operate with the closure head and externally in order to co-operate with the said main part; in particular, the associated toothings are in the form of axial flutings, the said flutings being additionally such that the connection between the closure cap and the closure head occurs before the connection between the said cap and the main part of the cap.

Preferably, for one or other of the two above-mentioned embodiments, it is particularly advantageous that the screw cap has at the lower end a tamperproofing ring snap-locking onto the main body when the said assembly is being put together, the said tamperproofing ring being toothed internally in order to co-operate with a homologous outer toothing of the said main body, both the upper and lower connections by associated toothings to the said screw cap being homothetic in order to prevent any twisting of the closure head when the said assembly is being put together, the lower connection additionally providing for a centring of the said screw cap allowing the upper connection to be positioned without risk of twisting of the said closure head.

In accordance with another particularly advantageous embodiment making it possible to obtain a completely satisfactory drop formation, the upper part of the main body has on the inside a flow rate restriction system permitting control of the drop formation, the said system being positioned substantially according to the axis of the said main body, and being held in position by a constricted portion of the upper part of the said main body, the said upper part extending, beyond the said system, via the dispensing portion surmounted by the tear-off closure head.

According to a first variant, the flow rate restriction system is a small capillary tube whose central channel is delimited by two end facets.

In this case, the capillary tube is cylindrical and has a circular cross-section, or else is cylindrical and has a figure eight cross-section. This is advantageous insofar as the capillary tubes are inexpensive and are available in long lengths, which makes it possible to automate manufacture easily.

Again, preferably, the upper facet of the capillary tube is inclined relative to the axis of the central channel: the liquid jet can thus be deflected towards the wall of the main body in such a way that the jet broken in this way is more easily transformed into a drop (a non-inclined facet would introduce a risk of having a small jet not forming a drop).

Preferably, the upper part of the main body has, beyond the upper facet of the capillary tube, a cylindrical bore wider than the capillary tube, in order to improve the control of the size of the drop of liquid during the use of the said packaging assembly.

Advantageously, in this case, the dispensing portion of the main body is connected to the closure head, beyond a rounded upper shoulder terminating the cylindrical bore, by an annular zone forming a rim conferring upon the main body a certain degree of elastic deformation in an axial direction; in particular, the annular zone forming a rim is connected to the closure head via a necking, making it possible, after the said closure head has been broken, to seal the main body by means of axial pressure.

According to another variant, the flow rate restriction system is a small capillary tube whose central channel is delimited by two end facets and whose lower end is capped by a filter held in position by the constricted portion of the upper part of the main body, the mesh of the said filter being chosen with respect to the desired degree of flow rate restriction.

Advantageously, in this case, the edge of the filter capping the capillary tube is wedged between the said tube and the constricted portion of the upper part of the main body. Again, preferably, the capillary tube is cylindrical and of circular cross-section and/or the upper facet of the capillary tube is inclined relative to the axis of the central channel.

According to another variant, the flow rate restriction system comprises at least one porous tube curved into a horseshoe shape, of which the two ends, arranged in an adjacent manner and parallel to the axis of the main body, are held in position by the constricted portion of the upper part of the said main body.

According to yet another variant, the flow rate restriction system is a porous cylindrical block arranged coaxially to the main body and held in position by the constricted portion of the upper part of the said main body, the said constricted portion surrounding the entire lateral surface of the said block; in particular, the porous cylindrical block is preferably made of sintered polypropylene or polyethylene.

According to yet another variant, the flow rate restriction system is a cylindrical core fluted longitudinally or made in the form of a porous tube with a central channel, arranged coaxial to the main body, and of which the useful lateral surface is surrounded by a filter held in position by the constricted portion of the upper part of the main body by being wedged between the said portion and the fluted cylindrical core at the level of each of the ends of the said core, the mesh of the said filter being chosen with respect to the desired degree of flow rate restriction.

Advantageously, the constricted portion of the upper part of the main body has a central crushing at the level of the lower end of the fluted cylindrical core, this simultaneously ensuring the holding of the said core and defining two axial passages permitting the movement of the liquid towards the useful lateral surface surrounded by the filter. In particular, the filter is wound, through slightly more than one turn, around the fluted cylindrical core in order to afford an axial covering zone, or else the filter is made up of two sheets whose opposite edges are connected, the two longitudinal lips being folded down.

It is also advantageous in the different variants mentioned above for the upper part of the main body to have, beyond the upper end of the flow rate restriction system, a wider cylindrical bore, in order to improve the control of the size of the drop of liquid during the use of the said assembly.

Also, preferably, the dispensing portion of the main body is connected to the closure head, beyond a rounded upper shoulder, via an annular zone widening conically. Advantageously, the upper part of the main body terminates in a dispensing end-piece surmounted by a hat-shaped closure head which is wider than the said end-piece; in particular, the closure head has an outer surface externally toothed in such a way as to co-operate with a homologous inner toothing of the screw cap in order to detach the said closure head by unscrewing the said cap, the associated toothings being in the form of axial flutings.

Also preferably, the packaging assembly comprises a snap-locking means between the screw cap and the closure head, allowing the said closure head to be retained once torn off in the said cap after unscrewing of the latter: for example, the snap-locking means essentially consists of an upper point in the form of an arrow surmounting the closure head, able to co-operate with transverse lugs or a transverse base of the screw cap.

Advantageously, the screw cap is monobloc and has, at the lower end, a toothing which can move aside upon fitting by pressure, when the said assembly is being put together, in contact with the outer threading of the upper part of the main body; in particular, the screw cap has at the lower end a tamperproofing ring snap-locking onto the main body when the said assembly is being put together.

The invention also relates to a method for manufacturing a sterile packaging assembly made of plastic material, of the type mentioned above, this method being characterized by the fact that it comprises the following stages:
- the lower part of a main body designed to contain the liquid to be dispensed is made by blowing in a main mould, then the said main body is filled;
- the upper part of the main body is then made in a head mould;
- a closure head is finally made in a sealing mould, in order to terminate the main body;
- a screw cap is put into position;
- a coupling connection is made between the outer surface of the closure head and the inner adjacent surface of the screw cap, which has the effect of rotationally coupling the said closure head to the said cap.

According to a first mode of implementation of the method, the coupling connection is made after the positioning of the cap by screwing, by gluing or welding carried out between the opposite surfaces concerned.

According to another mode of implementation of the method, the coupling connection is formed directly during the positioning of the cap by snap-locking of homologous axial flutings, the said positioning being effected by axial fitting by virtue of a flexible internal thread which can move aside.

Finally, it is advantageous if, after the stage of production of the lower part of the main body by blow moulding, and before the stage of production of the upper part of the said main body, the method comprises the following successive stages:

> a flow rate restriction system is positioned substantially following the axis of the main body by means of a temporary support;
>
> the flow rate restriction system is held in place in the head mould, whose closure clamps a portion of the main body onto the said system.

Other characteristics and advantages of the invention will appear more clearly in the light of the following description and the attached drawings, concerning particular embodiments, with reference to the figures in which:

FIGS. 2A and 2B illustrate two variants of the above assembly, in which a flow rate restriction system in the form of a small cylindrical capillary tube is also provided in order to improve the drop formation after rupturing of the tear-off head;

FIG. 3 illustrates another variant, in which the capillary tube has a figure eight cross-section, as emerges from FIG. 4, of which FIG. 3 is a section along III-III (more detailed);

FIGS. 5 and 6 illustrate the gripping mandrel used in this case in order to position the capillary tube with figure eight cross-section;

FIGS. 11a and 11b are diagrammatic sections illustrating the procedure for manufacturing an assembly of the above type, here comprising a flow rate restriction system, FIG. 11a corresponding to the preliminary blowing and filling stations, and FIG. 11b corresponding to the subsequent stations for positioning of the capillary tube and final sealing;

FIG. 15 illustrates a section through another variant with the same type of coupling as above between the closure head and screw cap, in which the flow rate restriction system is a fluted cylindrical core whose useful surface is surrounded by a filter (the main body has a central crushing at the level of the lower end of the surrounded core, as can be seen more clearly by referring also to the sectional side view in FIG. 16);

FIGS. 17 to 20 are sections, respectively along XVII—XVII, XVIII—XVIII, XIX—XIX, and XX—XX in FIG. 15, permitting a better understanding of the particular configuration of the body of the assembly;

FIGS. 21 and 22 are sections illustrating the covering of the fluted core by means of a filter, respectively with one covering or two folded-down lips;

FIG. 23 is a diagrammatic view of an apparatus facilitating the cutting and the gripping of capillary tube sections.

Figure 1:
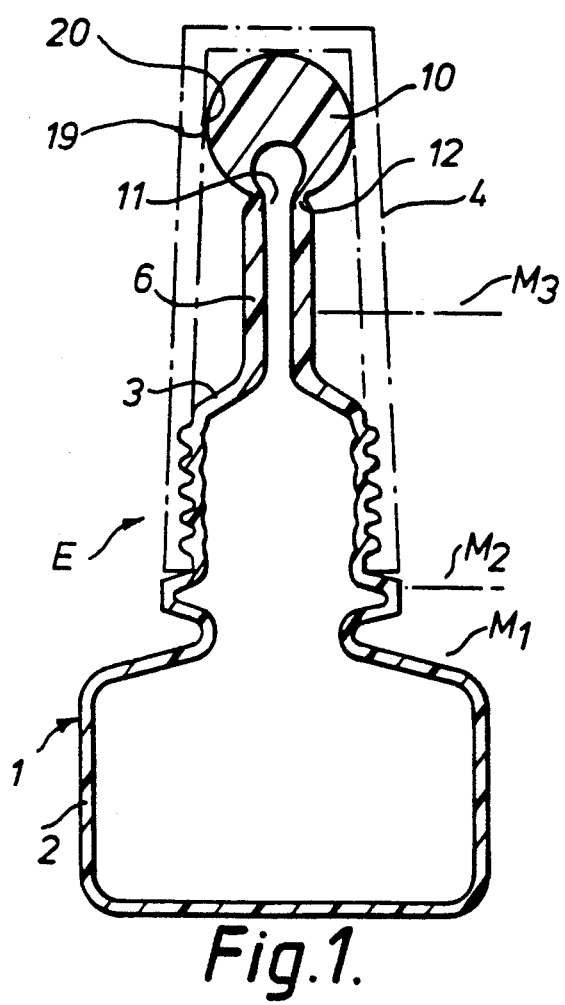
FIG. 1 is an axial section through a sterile packaging assembly according to the invention, in which assembly the closure head is of a generally flat shape and is coupled by friction to the screw cap.
Figure 7:
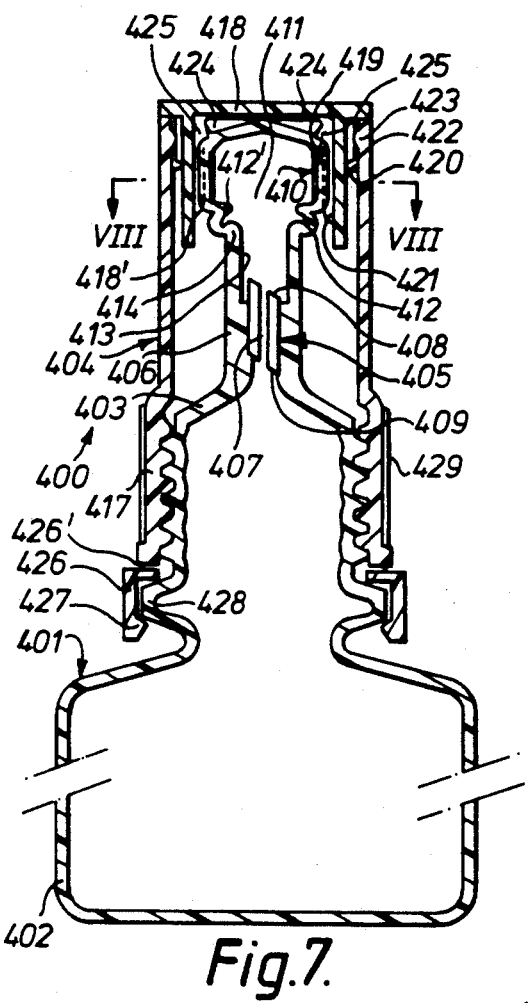
FIG. 7 illustrates another variant, in which the closure head is toothed externally for a better rotational coupling with the screw cap, additionally with a snap-locking means allowing the closure head (lacuna) once torn off in the cap after unscrewing the latter, the said screw cap here being in two parts.
Figure 8:
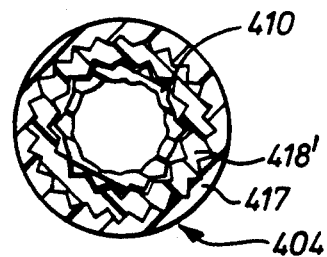
FIG. 8 is a section along VIII—VIII in FIG. 7, illustrating the double rotational connection provided at the level of the closure head, here by axial flutings.

FIG. 1 illustrates a sterile packaging assembly according to the invention, allowing a liquid to be dispensed in drops. The packaging assembly E comprises a main body 1 made of plastic material, whose lower part 2 constitutes an actual bottle part capable of receiving the liquid to be dispensed, and whose upper part 3 is threaded externally in order to receive a screw cap 4.

According to an important aspect of the invention, the upper part 3 ends in a narrower elongate neck 6 constituting a dispensing portion, the said dispensing portion being surmounted by a closure head 10 which can be torn off in order to define a dispensing orifice 11, and means for rotational coupling are provided between the outer surface of the closure head 10 and the adjacent inner surface of the screw cap 4, the said means making it possible to detach the said closure head by unscrewing the said cap at the time of the first use of the packaging assembly.

The closure head 10 is here wider than the elongate neck 6 and has a general flattened shape, presenting an outer surface 19 adjacent to the opposite inner surface 20 of the screw cap 4. A rigid connection, preferably by gluing or laser welding carried out between the opposite surfaces after the positioning of the screw cap 4, is additionally provided in order to define the coupling between the said closure head and the said screw cap.

It is possible in this way to produce a packaging assembly whose structure is very simple, without the least risk of defective leakproofness capable of spoiling the sterility (the closure head 10 is in fact connected to the elongate neck 6 by means of an annular zone 12 forming a continuous rim, the tearing-off being effected at the level of this annular zone 12 upon unscrewing of the cap 4). Moreover, the first use is particularly simple for the patient because the latter has only to perform a natural maneuver by unscrewing the cap.

The gluing or laser-welding technique is, however, difficult to implement and is relatively expensive, which may lead to the selection of another equivalent technique using a rotational coupling by means of axial toothings, as will be described hereinafter, particularly with reference to the FIGS. 7 to 10 and 12 to 16.

The variants in FIGS. 2A and 2B comprise an analogous arrangement as far as the closure head and screw cap are concerned, so that the homologous parts will be allocated the same references, increased respectively by one hundred and two hundred.

The packaging assembly 100 in FIG. 2A thus comprises a main body 101, with a lower part 102 and an upper part 103, the latter being surmounted by a tear-off closure head 110 and being threaded externally in order to receive a screw cap 104.

The packaging assembly 100 in FIG. 2A differs from the packaging assembly E described above in that the upper part 103 of the main body 101 has on the inside a flow rate restriction system 105 making it possible to control the drop formation, the said system being positioned substantially following the axis of the main body 101 and being held in position by a constricted portion 106 of the upper part 103 of the said main body.

The flow rate restriction system is of the type consisting of a small capillary tube 105 whose central channel 107 is delimited by two end facets 108, 109. The capillary tube 105 is here cylindrical and of circular cross-section, but this of course constitutes only one example, as will be seen hereinafter. Such an embodiment is particularly advantageous insofar as the capillary tubes are inexpensive and are available in long lengths, this making it possible to easily automate the manufacturing, as will be described hereinafter.

As can be seen in FIG. 2A, the upper facet 108 of the capillary tube 105 is inclined relative to the axis of the central channel 107 (the lower facet 109 is also inclined here, but this results only from a simplification of the method of manufacture of the small capillary tube): for this reason the liquid jet can thus be deflected towards the wall of the main body 101, in such a way that the jet thus broken is converted more easily into a drop.

The closure head 110 in the form of a flat disc is connected, as before, to the dispensing portion of the main body 101 by way of an annular zone forming a rim 112, this improving the geometry at the level of the dispensing orifice 111: the screw cap 104, attached by gluing or welding to the closure head 110 after screwing of the said cap onto the main body 101, makes it possible to pull the closure head 110 upon unscrewing of the cap 104 and to provoke a tearing at the level of the annular zone 112, which permits freeing of a central orifice 111 for dispensing the liquid.

In FIGS. 1 and 2A (as well as in FIG. 2B which relates to a variant described hereinafter), dot-and-dash lines indicate diagrammatically the presence of the moulds used to manufacture the packaging assembly: thus, the main mould M1, the head mould M2 (which constitutes in particular a mould for holding the capillary tube in the case of FIG. 2A), and finally the sealing mould M3. The stages typical of the manufacturing procedure will be dealt with in greater detail later, with reference to FIGS. 11a and 11b.

The major advantages afforded by such an arrangement can already be seen: the small capillary tube 105 makes it possible to obtain easily a regular drop formation without a jet, and the arrangement with a tear-off head 110 preserves perfectly the leakproofness and sterility of the system. Moreover, the capillary tube is inexpensive (it will be possible to use, for example, capillary tubes extruded in a long length, of the type used for aerosols): by way of indication, a small capillary tube of this type is approximately thirty times cheaper than an injected end-piece/stopper subassembly used in certain known techniques mentioned hereinabove.

The drop formation is controlled perfectly here: as regards the flow rate, the flow rate restriction system consisting here of the capillary tube 105 is particularly effective insofar as it is easy to form a microchannel 107 in such a tube; as regards the size of the drop, which is essentially a function of the geometrical shape of the dispensing end, the results are on the whole very satisfactory.

It should be noted that the axial wedging of the small capillary tube 105 is in fact not in any way critical for a satisfactory drop-formation quality. This facilitates the manufacturing, and in particular the positioning of the capillary tube by the constricted portion 106 (such a positioning is in fact equivalent to welding, especially if materials of the same nature are used, such as polyethylene).

However, it should be noted that, if a packaging assembly such as that illustrated in FIG. 2A is produced, the quality of the result is perhaps not optimal as far as the size of the drop is concerned, and this essentially on account of the presence of a break line at the site of the formation of the drop.

The variant illustrated in FIG. 2B aims specifically to overcome this drawback. The packaging assembly 200 has a large number of parts in common with the packaging assembly 100 which has just been described, and these common parts will thus be allocated the same references as above, increased by one hundred.

The essential difference compared with the previous variant lies in the geometry of the dispensing portion of the main body 201: it will in fact be seen that the upper part 203 of the main body 201 has, beyond the upper facet 208 of the capillary tube 205, a cylindrical bore 213 which is wider than the capillary tube, this making it possible to improve very substantially the control of the size of the drop of liquid, when the said packaging assembly is used, by means of the careful geometry at the level of the dispensing orifice 211. An annular rim 214 terminating the cylindrical bore 213 will in fact be seen, beyond which there is the annular zone 212 serving as the connection between the tear-off head 210 and the main body 201.

The improvement in the geometry very substantially improves the precision of the drop, this constituting a major advantage despite the increase in the size of this drop, which will lead to the dispensing of a quantity of liquid which sometimes exceeds the quantity strictly necessary. It should also be noted that the formation of the cylindrical bore 213 and of the upper annular rim 214 naturally complicates manufacture somewhat (it will then be necessary to provide an appropriately designed gripping system, such as that which will be described later).

The variant illustrated in FIG. 3 makes it possible to overcome the problem of the size of the drop if it is desired to have a drop of small volume.

The packaging assembly 300 comprises, as above, a main body 301 with an externally threaded upper part 303, the said part extending by way of a constricted portion 306 serving for holding a flow rate restriction system 305 in position. The essential difference compared to the previously described embodiment lies in the particular design of the flow rate restriction system 305, which here consists of a small cylindrical capillary tube having a figure eight cross-section (the section in FIG. 4 makes this particular cross-sectional form clearer). This cross-section in fact makes it possible to benefit at one and the same time from the advantages of a small and a large outer diameter: the small diameter makes it possible to obtain a drop of a small size, and the large diameter in the other direction makes it possible to retain sufficient material for a good mechanical behaviour and great ease of gripping during manufacture. In addition, as above, it will be advantageous to have the upper facet 308 of the capillary tube 305 inclined relative to the axis of the central channel 307. Furthermore, as in the variant in FIG. 2B, there is a cylindrical bore 313 beyond the capillary tube 305, this terminating in an annular rim 314 at the level of the dispensing orifice 311.

FIGS. 5 and 6 show the lower end of an endpiece 315 serving as a gripping system in the case of a capillary tube of the type of the tube 305 described above. The end-piece 315 has in fact an annular shoulder 316', whose function is to define the annular rim 314 during moulding, a cylindrical portion of smaller diameter 316" whose function is to define the inner cylindrical bore 313, and finally two lugs 316 making it possible to clasp a capillary section 305 at the level of its part of smaller diameter.

It goes without saying that, in certain cases, it will prove advantageous to provide an external threading on the part 306 of the main body 301, in order to make it possible to screw on a stopper after separation of the head 310. FIG. 4 also permits an appreciation of the particular shape of the part 306 of the main body, this resulting from the figure eight cross-section of the capillary tube 305: it should also be noted that the section in FIG. 3 comprises a left half-section corresponding to a section made in a plane perpendicular to the plane of opening of the mould M2, while the right half-section corresponds to a section in the plane of opening of the said mould.

FIGS. 7 to 10 illustrate variants of the invention in which the upper part of the main body is surmounted by a closure head having an externally toothed outer surface, in such a way as to co-operate with a homologous inner toothing of the screw cap in order to detach the said closure head by unscrewing of the said cap.

This solution is less difficult to implement than the solution mentioned above, with gluing or welding at the level of the opposite surfaces.

It should also be remembered that, in the known techniques using a tear-off head, the packaging assembly was not in general resealable, which necessitated the use of a separate stopper, pre-assembled or otherwise. This gave rise to a succession of operations sometimes difficult for certain patients, who had to successively open a cap, tear off the head, remove this head, then reseal the assembly. In this case the specialists encountered a well-known problem: if the tear-off head was of a small diameter, this involved difficulties in handling, and if the tear-off head was of a wide diameter, then although handling was more straightforward, this entailed the presence of a pre-assembled separate capsule or stopper.

Thus, in accordance with an important aspect of the invention, it is anticipated that the screw cap will perform a double function, that is to say not only ensure the initial opening by tearing-off of the head, but also the closure of the packaging assembly. However, it should be noted that an additional difficulty has to be overcome in the case of a co-operation by toothings, namely that of ensuring that the head cannot under any circumstances have been torn off before the unscrewing of the cap is carried out at the time of the first use of the packaging assembly. Measures must therefore be taken to reduce the stresses which may be communicated by the cap to the tear-off head during assembly, and in particular to avoid the torsional stresses.

The packaging assembly 400 illustrated in FIGS/ 7 and 8 comprises parts in common with the assemblies described previously, and so, in order to avoid overloading the description, these parts will be designated by references in the four hundreds.

The dispensing portion of the main body 401 is connected to the closure head 410, beyond a rounded upper shoulder 414 terminating the cylindrical bore 413, by means of an annular zone forming a rim 412 giving the main body 401 a certain degree of elastic deformation in an axial direction. The annular zone forming the rim 412 is moreover connected to the closure head 410 by a necking 412' making it possible, after breaking off the said closure head, to seal the main body 401 by means of axial pressure. Moreover, the upper part 403 of the main body 401 ends in a narrower elongate neck constituting the dispensing portion, being surmounted by a closure head 410 wider than the said elongate neck, and this closure head 410 has an externally toothed outer surface 419 in such a way as to co-operate with a homologous inner toothing 421 of the screw cap 404 in order to detach the said closure head by unscrewing of the said cap. The associated toothings of the closure head 410 and of the screw cap 404 will advantageously be in the form of axial flutings.

The screw cap 404 is here in two parts 417, 418 which can be connected to each other by axial snaplocking, namely a main part 417 threaded internally in order to screw normally onto the upper part 403 of the main body 401 when the said assembly is being put together, and a second part 418 forming a closure cap, this second part presenting the toothed portion co-operating with the outer toothing of the closure head 410. It is of course appropriate in this case to provide for a rotational drive connection between the two parts constituting the screw cap. Thus, the second part forming the closure cap 418 here has a cylindrical sleeve 418' penetrating into the main part 417 of the cap 404, the said sleeve being toothed internally in order to cooperate with the closure head 410 (axial flutings 421 of the sleeve 418' co-operating with homologous axial flutings 419 on the closure head 410), and externally in order to co-operate with the main part 417 (axial flutings 422 of the sleeve 418, and homologous axial flutings 420 on the main part 417). It will be noted that lugs 423 are provided internally in the main part 417 in order to permit an axial snap-locking with a homologous groove in the second part forming the closure cap 418.

Moreover, it is advantageous also to provide a snap-locking means between the screw cap 404 and the closure head 410, making it possible to retain the said closure head once torn-off in the said cap after unscrewing of the latter. The snap-locking means here essentially consists of radial fins 424 surmounting the closure head 410, and of which the radially outside edge forms a lug co-operating with an annular rim 425 formed in the inner surface of the screw cap 404. Two radial fins 424 will preferably be provided, situated in the joint plane of the mould used for producing the main body 401. In this case it will be preferable to ensure that the associated toothings are in the form of axial flutings organized in such a way that the connection between the closure cap 418 and the closure head 410 takes place before the connection between the said closure cap and the main part 417 of the screw cap 404.

Furthermore, the main part 417 of the screw cap 404 has at the lower end a tamperproofing ring 426 which is toothed internally (preferably with axial flutings not shown here) and which is connected to it by bars 426', the said ring snap-locking by means of its circular groove 427 on a swelling 428 of the main body 401, when the said assembly is being put together, in order to cooperate with a homologous outer toothing of the main body 401 when the packaging assembly is put together. In this case it is expedient to ensure that the two upper and lower connections by toothings associated with the screw cap 404 are homothetic in order to avoid any twisting of the closure head 410 when the packaging assembly is being put together, the lower connection additionally affording a centering the screw cap 404 permitting correct positioning of the upper connection without risk of twisting of the said closure head 410.

Once the main body 401 has been produced, with its capillary tube 405 and its externally toothed tearoff closure head 410, it is appropriate to proceed with the fitting of the screw cap 404: first, the main part 417 is positioned on the main body 401 until snap-locking of the tamperproofing ring 426, then the part 418 forming the closure cap is put into position, the latter being simply fitted on axially, this automatically bringing into engagement the two rotational coupling connections, and this without imparting any torsional stress to the closure head 410. Once the closure cap 418 has been clipped onto the main part 417, the said cap and the closure head 410 are known to have snap-locked by means of the radial fins of the closure head, the elasticity in an axial direction confered by the connection rim 412 preserving the flexibility of the system. It should be noted that this arrangement makes it possible, in addition to preserving the tamperproofing, to carry out an axial centering of the closure head 410: this centering takes place progressively, initially by the closure cap 418 on the closure head 410 (the angle corresponds substantially here to 1/12th of a turn), and then by the main part 417 on the above subassembly (the angle in question is then approximately 1/48th of a turn), this making it possible to avoid any transmission of torsional stresses to the closure head 410.

A practical advantage of a two-part embodiment of the screw cap 404 should be noted, namely that of providing two different colours for these two parts, this permitting a rapid identification of the packaging assembly by the patient. The handling will be further facilitated by providing longitudinal ribs 429 on the outer surface of the main part 417 of the screw cap 404.

It should be remembered that, after the first unscrewing of the cap 404 and separation of the head 410, the renecking 412' of the said head which, it will be remembered, is held inside the screw cap, makes it possible, upon subsequent re-screwing, to ensure the leakproofness of the packaging assembly by means of its bearing on the annular rim 414.

Figure 10:
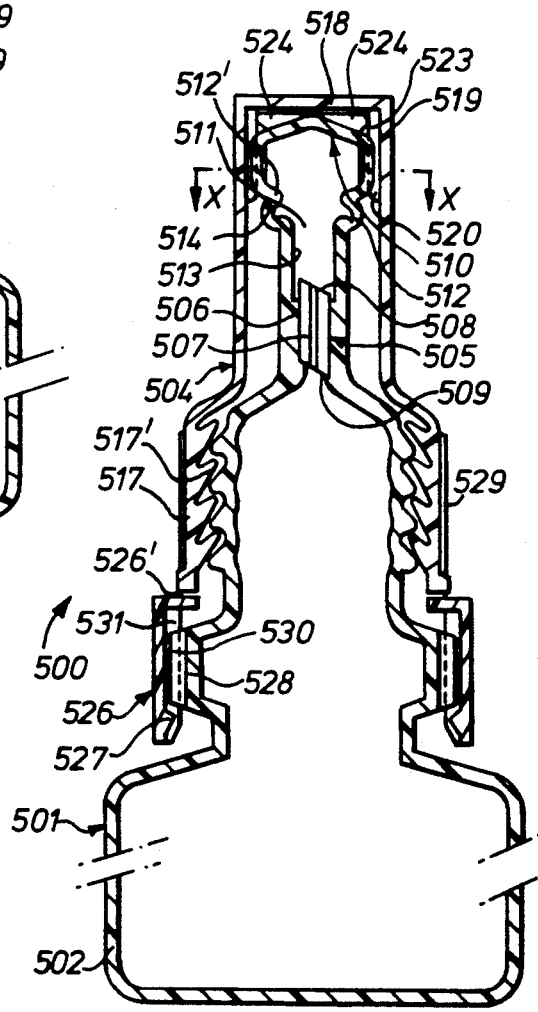
FIG. 10 is a section along X—X in FIG. 9, illustrating the rotational connection by axial flutings.
Figure 9:
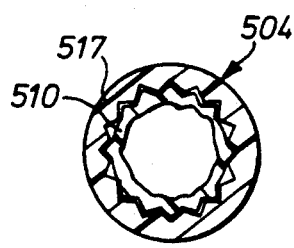
FIG. 9 illustrates a variant of the above assembly, but with a monobloc screw cap, which can then be fitted on axially during assembly (the cap has at the lower end a flexible thread which moves aside during this fitting)

FIGS. 9 and 10 illustrate a variant of (lacuna) embodiment which has just been described, a variant in which the screw cap is no longer made up of two parts, but consists of a single piece.

In order not to overload the description, the identical or homologous parts will be allocated the same references as above, increased by one hundred.

The packaging assembly 500 thus comprises a screw cap 504 which is monobloc, that is to say the upper part 518 forms a single piece with the main part 517. This somewhat simplifies the production of the connection between the screw cap 504 and the closure head 510: it suffices in fact to provide axial flutings 520 on the inner surface of the screw cap, in order to co-operate with the outer toothing 519 of the closure head 510. In addition, there is also only a single axial snap-locking system at this level, namely that formed by a rim 523 of the screw cap and the lugs provided at the end of the radial fins 524 borne by the closure head 510.

The lower threading of the cap 504 is moreover modified in order to facilitate the positioning of the said cap on the main body 501. For this purpose, the screw cap 504 has at the lower end a flexible thread 517' which can move aside upon fitting by pressure, when the packaging assembly is being put together, in contact with the outer threading of the upper part 503 of the main body 501. It should also be noted that the screw cap 504 has at the lower end a tamperproofing ring 526 which is threaded internally (preferably with axial flutings 531) in order to co-operate with a homologous outer toothing 530 of the main body 501. It is in this case preferable to ensure that the two upper and lower connections to the said screw cap by associated toothings (connections by flutings 519 and 520 in the upper part, and 530, 531 in the lower part) are homothetic in order to avoid any twisting of the closure head when the said assembly is being put together, the lower connection additionally affording a centring of the screw cap 504, making it possible to position the upper connection without risk of twisting of the closure head 510.

Once the main body 501 has been formed, it then suffices simply to fit the cap 504 on axially by pressure in order to obtain the different coupling connections, and this without risk of imparting the torsional stresses to the closure head 510. As above, it will additionally be advantageous to ensure that the connection in the lower part (that is to say at the level of the tamperproofing ring) takes place before the connection in the upper part (at the level of the closure head).

In the two variants which have just been described with reference to FIGS. 7 to 10, the presence of clearances in an axial direction between the screw cap and the upper part of the main body will be noted, these clearances being necessary in order to be able to reclose the packaging assembly after the first use.

FIGS. 11a and 11b illustrate diagrammatically the procedure for manufacturing an assembly of that type illustrated in FIG. 2A, FIG. 11a corresponding to the preliminary stations of blowing and filling, and FIG. 11b to the subsequent stations of positioning the capillary tube and final sealing. However, it goes without saying that, in the most general case, that is to say for a packaging assembly not provided with a flow rate restriction system, the manufacturing procedure will not comprise the stages of positioning and setting the flow rate restriction system.

A set of four moulds can be seen, comprising the main mould M1, the head mould M2, the sealing mould M3, and finally the pieces for holding the pre-form M4. It goes without saying that the members M2, M3, M4 comprise means for vacuum suction in a manner which is entirely conventional in this field. A slide T can also be seen, which is movable in translation or in rotation and supports, on the one hand, a mandrel 132 assigned to the functions of blowing the lower part of the packaging assembly and filling the latter via the associated rod 133, and on the other hand an end-piece 115 of the gripping system assigned to the gripping of the capillary tube constituting the flow rate restriction system. This end-piece 115 comprises a central channel 115' permitting a vacuum suction to be carried out by virtue of a connection to an external source, not shown here, and has at the lower end lugs 116 for gripping the capillary tube. The mandrel 132 and the end-piece 115 can of course effect a translational movement in a vertical direction. An assembly P can also be seen which forms a clamp for positioning and advancing the capillary tube, the latter arriving in the form of a continuous strand 105', with a knife C making a cut at the desired length of the capillary tube section.

In the position in FIG. 11a, the blowing and filling stages are carried out using the mandrel 132, and, at the other station, the end-piece 115 is lowered, upon advance of the capillary tube, to cut the latter to the desired length, and to grip the cut section. The members are then brought into the position in FIG. 11b: the end-piece 115 then allows the capillary tube 105 to be set at the desired position, after which the head mould M2 is closed, this making it possible simultaneously to effect partial shaping of the upper part of the main body of the packaging assembly and to hold the capillary tube in place by means of the constricted portion 106. The final phase, not shown here, concerns the closure of the sealing mould M3, this making it possible to achieve shaping of the closure head of the packaging assembly after the end-piece of the gripping system has been raised. It goes without saying that the two stations will be organized to function in overlapping time, so that the automated procedure takes place with an optimum yield.

Figure 14:
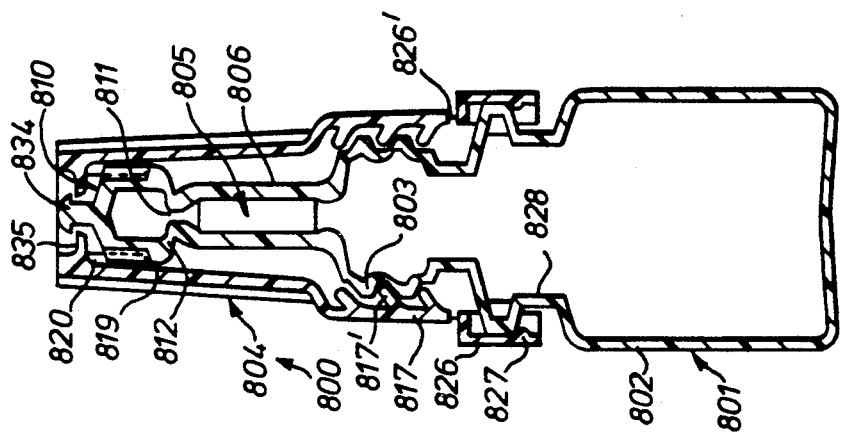
FIGS. 12 to 14 illustrate other variants in section, in which variants another snap-locking type is provided between the closure head and the screw cap, and in which the flow rate restriction system is, respectively, a capillary tube whose lower end is capped by a filter, a porous tube curved in the shape of a horseshoe, and a porous cylindrical block.
Figure 13:
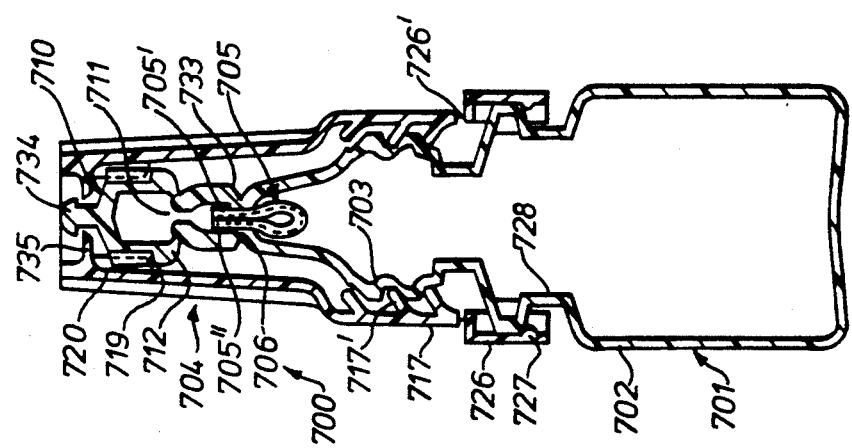
Figure 12:
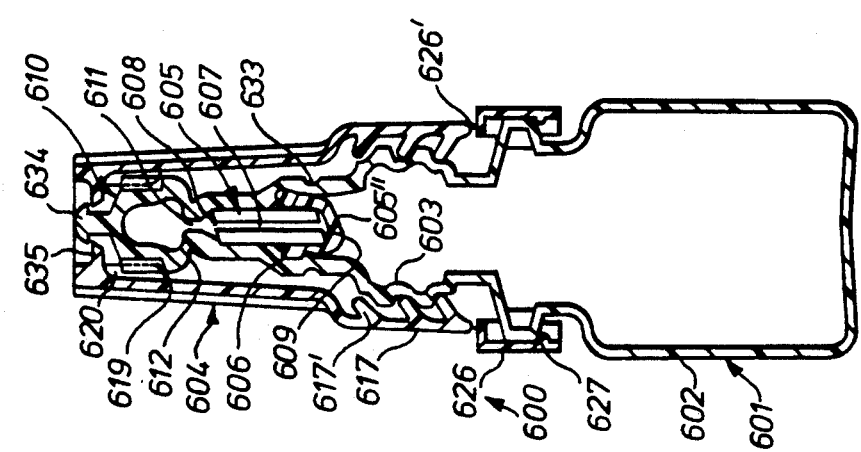

FIGS. 12 to 14 concern other variants of the invention, in which the flow rate restriction system differs substantially from the simple capillary tube of the variants described previously: these variants will show clearly that the invention is in no way limited to a particular type of flow rate restriction system, and that the latter can present a very varied structure.

The packaging assembly 600 illustrated in FIG. 12 comprises many parts which are identical or analogous to those of the variant described above with reference to FIGS. 9 and 10: in order to lighten the description, these parts will be allocated the same references increased by one hundred.

. The essential difference compared to the previous variant lies in the structure of the flow rate restriction system 605: the latter is in fact made up of a small capillary tube 605, (analogous to the capillary tubes described previously), whose central channel 607 is delimited by two end facets 608, 609, and whose lower end is capped by a filter 605,, held in position by the constricted portion 606 of the upper part of the main body 601, the mesh of the said filter being chosen with respect to the desired degree of flow rate restriction. It is of course advantageous to ensure that the edge of the filter 605" capping the capillary tube 605, is wedged between the said tube and the constricted portion 606 of the upper part of the main body 601. It is important to note that the filter 605" here performs a double function: it acts in the first instance as a flow rate restriction system (making it possible to obtain a low flow rate regardless of the pressure exerted by the patient on the main body of the packaging assembly), and it acts secondarily as a filter. By way of indication, it will be possible to use a relatively thin filter (with a thickness of less than 1 mm), optionally with an additional pre-filter layer tending to give it a better mechanical strength.

The presence of a groove 633 will be noted in the upper part of the main body at the level of the lateral wall of the filter 605" which must be firmly applied against the lateral surface of the lower end of the capillary tube 605'. In addition, and as above, the capillary tube 605' will be able to be cylindrical and of circular cross-section, with an upper facet 608 inclined relative to the axis of the central channel 607.

It will of course be possible for the upper part 603 of the main body 601 to have, beyond the upper end of the flow rate restriction system 605, a wider cylindrical bore in order to improve the control of the size of the drop of liquid during use of the said assembly.

Moreover, the dispensing portion of the main body 601 is connected to the closure head 610, beyond a rounded upper shoulder provided at the level of the dispensing orifice 611, by means of an annular zone 612 widening conically.

More precisely, the upper part 603 of the main body 601 terminates in a dispensing end-piece surmounted by a hat-shaped closure head 610 which is wider than the said end-piece. In addition, as in the previous variants, and in accordance with an essential aspect of the invention, the closure head 610 has an outer surface 619 toothed externally in order to co-operate with a homologous inner toothing 620 of the screw cap 604 in order to detach the said closure head by unscrewing of the said cap, the associated toothings preferably being in the form of axial flutings 619, 620.

Moreover, it is advantageous also to provide a snap-locking means between the screw cap 604 and the closure head 610, allowing the said closure head to be retained once torn off in the said cap after unscrewing of the latter. In this case, this snap-locking means essentially consists of an upper arrow-shaped point 634 surmounting the hat-shaped closure head, and able to co-operate with transverse lugs or a transverse base 635 of the screw cap 604.

Finally, the screw cap 604 is here monobloc, and has at the lower end a flexible thread 617, which can move aside upon fitting by pressure, when the said assembly is being put together, in contact with the outer threading of the upper part of the main body 601. The screw cap 604 has at the lower end an internally toothed tamper-proofing ring 626 snap-locking onto the main body 601 when the packaging assembly 600 is put together, in the same way as the ring 526 in the variant described previously, the arrangement of the two upper and lower connections by associated toothings being in particular homothetic in order to prevent any twisting of the closure head 610 when the said assembly is being put together.

The variant in FIG. 13 differs from the variant described previously in terms of the structure of the flow rate restriction system, so that, as above, the identical or homologous parts will be allocated the same references increased by one hundred.

The packaging assembly 700 thus comprises a flow rate restriction system 705 which is made in the form of at least one porous tube curved in the shape of a horseshoe (here a single tube), of which the two ends 705', 705", arranged adjacently and parallel to the axis of ted portion 706 of the upper part of the main body 701. To produce the curved porous tube use will preferably be made of sintered polypropylene or polyethylene.

FIG. 14 illustrates another variant in which the packaging assembly 800 comprises a flow rate restriction system 805 made in the form of a porous cylindrical block, arranged coaxially to the main body 801 and held in position by the constricted portion 806 of the upper part of the said main body, the said constricted portion surrounding the entire lateral surface of the said block. The porous cylindrical block 805 is preferably made of sintered polypropylene or polyethylene. The other members of the packaging assembly 800 are otherwise identical to those in the previous variant, so that the corresponding references have simply been increased by 100.

FIGS. 15 to 22 illustrate yet another variant, in which the packaging assembly 900 comprises a flow rate restriction system 905 made in the form of a cylindrical core 905', here fluted longitudinally (the core could also be made in the form of a porous tube of high porosity or a tube perforated radially, whose central channel would provide for the escape of the liquid in the axis of the said tube, while the abovementioned flutings would provide for an axial escape in the periphery of the core), arranged coaxially to the main body 901, and whose useful lateral surface is surrounded by a filter 905" held in position by the constricted portion 906 and the upper part of the main body by being wedged between the said portion and the fluted cylindrical core at the level of each of the ends of the said core, the mesh of the said filter being chosen, as in the variant in FIG. 12, with respect to the desired degree of flow rate restriction.

The main body in the packaging assembly 900 is, however, modified compared to the variants described previously insofar as the constricted portion 906 of the upper part of the said main body has a central crushing 906" at the level of the lower end of the fluted cylindrical core 905', which at one and the same time provides for the holding of the said cora and defines two axial passages 936 permitting the movement of the liquid towards the useful lateral surface surrounded by the filter 905'. The sectional views associated with FIG. 15 permit a better understanding of the organization of the modified structure of the main body, and in particular the arrangement of the two axial passages 936.

FIG. 21 illustrates a variant in which the filter 905" is wound round the fluted cylindrical core 905' through slightly more than one turn, in such a way as to provide an axial covering zone 905'''. FIG. 22 illustrates another variant, in which the filter 905" is made from two sheets whose opposite edges are connected, the two longitudinal lips thus defined 905'''$_1$, 905''$_2$ being folded down against the fluted cylindrical core 905'.

It goes without saying that it will be possible for the cylindrical core 905' to have a very variable cross-sectional form (for example an oval form, star-shaped form, etc.). As regards the materials constituting these cylindrical cores, it will be possible to use any material suitable for extrusion, such as polyethylene, polypropylene, or a polyamide. As regards the filter 905" surrounding the cylindrical core 905', a plastic material (preferably sintered polypropylene or polyethylene) may be used, or else metal or glass.

Such an arrangement permits a very advantageous ratio between the useful surface for flow rate restriction and the size.

Finally, FIG. 23 illustrates, in a diagrammatic view, an apparatus used in the particular case of a packaging assembly comprising a flow rate restriction system, for example here in the form of a small capillary tube: this apparatus in fact makes it possible to easily cut and grip the capillary tube sections, and this regardless of the shape of the cross-section of the latter.

The apparatus 150 essentially consists of a fixed body 170 in which there is arranged a rotary barrel 152 with an essentially horizontal axis. On the left of the figure, a fixed clamping assembly can be seen which consists of a lower jaw 151 (which is in fact here an extension of the apparatus body 170) and of an upper jaw 153. Also provided is a movable clamping assembly consisting of an upper jaw 154 and a lower jaw 155: this movable clamping assembly thus permits the advance of the capillary tube 105' presented in the form of a continuous tube of great length. As for the barrel 152, it comprises a bore 152' used to receive a length of capillary tube, until the latter abuts against a feeler 159 mounted movable in translation in its housing. A feeler brake 163 is also provided, held in a bearing position against the feeler 159 by way of a spring 164 whose pressure of application can be regulated by way of a screw 165. The apparatus body 170 comprises, in the lower part, a feeler pusher 161, here in the form of a rack whose movement is controlled by a pusher control 162 in the form of a toothed wheel. In the upper part of the apparatus body there is an outlet orifice 158 with whose axis the endpiece of the gripping system 105 is aligned with its suction channel 115' coaxial to the said orifice. The apparatus body 170 also comprises a fixed knife C, fixed by a bolt 156, the said knife being oriented in such a way that the rotation of the barrel 152 automatically produces a cutting of a capillary tube section in a facet inclined relative to the axis of the said tube, that is to say relative to the central microchannel of the latter. This explains why the end facet 159' of the feeler 159, against which the conveyed capillary tube 105' comes into abutment, is also inclined correspondingly. Finally, there is a suction means 157 arranged in the apparatus body 170 and used for the suction of the particles from cutting.

The function of the apparatus 150 involves the following successive stages:

advance of the capillary tube 105': during the phase of the advance of the movable clamping assembly, the jaws 151, 153 of the fixed clamping assembly remain open, while the jaws 154, 155 of the movable clamping assembly are closed;

checking of the presence and the suitable position of the capillary tube: the capillary tube 105' pushes the feeler 159, the position of the said feeler being detected by the positional sensor 160, this position being stable by virtue of the feeler brake 163;

rotation of the barrel and cutting of the capillary tube: the barrel 152 here turns in the clockwise direction, rotating by a quarter of a turn, this effecting automatically the cutting of a capillary tube section; the cut end then passes in front of the suction means 157, so that the particles generated are automatically removed;

gripping of the capillary tube: as soon as the capillary tube 105' is in its vertical position, that is to say coaxial with the outlet orifice 158, the end-piece of the gripping system 115 moves down into the apparatus body 170, and the feeler pusher 161 is actuated by its control 162 in such a way as to push the capillary tube section upwards, this automatically effecting the gripping of the said section by the end-piece 115 of the gripping system, the capillary tube being held by the elasticity of the end of the end-piece, or better still by a vacuum-operated gripping system by virtue of the presence of a suction channel 115' in the said endpiece.

It is of interest to note that the non-perpendicular cutting of the capillary tube results in slight deformations of the latter with flash, so that a deflection of the jet of liquid will automatically be obtained in the central channel of the capillary tube: this makes it absolutely certain to avoid any projection of liquid into the eye of the patient in the form of a jet, given that the jet of liquid is irremediably broken against the wall of the hole and permits formation of a liquid drop.

It goes without saying tat the apparatus 150 can be provided in a modular fashion, that is to say with a barrel comprising a plurality of housings 152' organized in its axis, in such a way that the rotation of the said barrel automatically produces the cutting of a plurality of capillary tube sections against the cutting blade C; it is thus easy to set up an automated procedure for handling a plurality of capillary tubes, using the same movements for controlling the jaws, the pushers, the rotation - cutting.

The means which have just been described make it easy to implement a method for manufacturing a sterile packaging assembly made of plastic material according to the invention, the said method comprising the following successive stages:

the lower part of a main body designed to contain the liquid to be dispensed is made by blowing in a main mould, then the said main body is filled;

the upper part of the main body is then made in a head mould;

a closure head is finally made in a sealing mould, in order to terminate the main body;

a screw cap is put into position;

a coupling connection is made between the outer surface of the closure head and the inner adjacent surface of the screw cap, which has the effect of rotationally coupling the said closure head to the said cap.

The coupling connection can be formed according to two types of techniques: in a first case, the coupling connection is produced after the positioning of the cap by screwing, by gluing or welding carried out between the opposite surfaces concerned; in another case, this coupling connection is formed directly during the positioning of the cap, by snap-locking of homologous axial flutings, the said positioning being effected by axial fitting by virtue of a flexible internal thread which can move aside.

In the particular case of a packaging assembly equipped with a flow rate restriction system, the method is then slightly modified in the sense that, after the stage of production of the lower part of the main body by blow moulding, and before the stage of production of the upper part of the said main body, the said method comprises the following successive stages:

a flow rate restriction system is positioned substantially following the axis of the main body by means of a temporary support;

the flow rate restriction system is held in place in the head mould, whose closure clamps a portion of the main body onto the said system.

The sterile packaging assembly according to the invention, as well as the associated manufacturing method, provide a large number of practical advantages. The possible solutions are much less expensive than the known solutions mentioned at the outset, and they make it possible to avoid the risks of defective leakproofness capable of spoiling the sterility of the packaging assembly. It is also possible to obtain a regular drop formation without a jet upon dispensing of the liquid. Moreover, whatever its embodiment, the packaging assembly remains simple to use for the patient, even in the case of elderly persons.

The invention thus represents a very significant advance compared to the known techniques: as regards the techniques including the insertion of an injected endpiece/stopper subassembly, the solution of the invention is much less expensive and avoids any risk of leakage. Additionally, as regards the techniques including the forming of a microchannel using u needle, it is possible to avoid any risk of blocking of the micro-hole insofar as the latter is integrated in a flow rate restriction system, and this solution secondarily makes it possible to easily re-use existing machines of the bottle pack type already having an insertion system.

The invention is not limited to the embodiment which has just been described but on the contrary encompasses any variant reproducing, with the equivalent means, the essential characteristics specified in the claims.

I claim:

1. A sterile packaging assembly allowing a liquid to be dispensed in drops, comprising a main body of plastic material whose upper part is threaded externally in order to receive a screw cap, said screw cap being in two parts, namely a main part threaded internally in order to be screwed normally, when said assembly is being put together, on said upper part of said main body, and a second part forming a closure cap and presenting an inner toothed portion, said main part and said second part being connectable to each other by means effecting an axial snap-locking, a rotary drive connection being additionally provided between said main part and said second part of said screw cap; said upper part of said main body ending in a narrower elongate neck constituting a dispensing portion, said dispensing portion being surmounted by a closure head which includes means to be torn off in order to define a dispensing orifice, said closure head having an outer surface externally toothed in such a way as to co-operate with the inner toothing of said second part of said screw cap, thereby allowing said closure head to be detached by unscrewing said cap upon the first use of said packaging assembly.

2. A packaging assembly according to claim 1, wherein the associated toothings of said closure head and said second part of said screw cap are in the form of axial flutings.

3. A packaging assembly according to claim 1, further comprising snap-locking means between the screw cap and the closure head, allowing said closure head to be retained, once torn off, in said cap after unscrewing of the latter.

4. A packaging assembly according to claim 1, wherein said second part of said screw cap, which forms the closure cap, has a cylindrical sleeve penetrating into said main part of said screw cap, said sleeve carrying said inner toothed portion to co-operate with the closure head, and additionally toothed externally as a part of the rotary drive connection in order to co-operate with said main part.

5. A packaging assembly according to claim 1, wherein said rotary drive connection between said main part and said second part of said screw cap comprises co-operating toothings therebetween.

* * * * *